(12) United States Patent
Berna et al.

(10) Patent No.: US 8,372,061 B2
(45) Date of Patent: *Feb. 12, 2013

(54) TREATMENT TIP INCISION TEMPLATE (75) Inventors: Norberto Berna, Rome (IT); Vincenzo Crudo, Arzignano (IT)

(73) Assignee: Noberto Berna, Rome (IT)

( * ) Notice: Subject to any disclaimer, the term of this patent is extended or adjusted under 35 U.S.C. 154(b) by 643 days.

This patent is subject to a terminal disclaimer.

(21) Appl. No.: 12/569,898

(22) Filed: Sep. 29, 2009

(65) Prior Publication Data

US 2010/0082032 A1 Apr. 1, 2010

Related U.S. Application Data (63) Continuation-in-part of application No. 10/843,476, filed on May 12, 2004, now Pat. No. 7,615,047.

(30) Foreign Application Priority Data

May 15, 2003 (IT) .............................. PD2003A0102

(51) Int. Cl.
*A61B 17/00* (2006.01)
*A61C 3/04* (2006.01)
(52) U.S. Cl. ................... 606/1; 433/29; 433/53; 604/22
(58) Field of Classification Search ................... 606/1, 2, 606/13, 53, 79, 80; 433/25, 29, 53; 604/19–22
See application file for complete search history.

(56) References Cited

U.S. PATENT DOCUMENTS

| 3,297,022 | A | 1/1967 | Wallace |
| 4,170,997 | A | 10/1979 | Pinnow et al. |
| 4,367,729 | A | 1/1983 | Ogiu |
| 4,438,773 | A | 3/1984 | Letterio |
| D342,136 | S | 12/1993 | Lafferty et al. |
| 5,527,182 | A | 6/1996 | Willoughby |
| 5,647,840 | A | 7/1997 | D'Amelio et al. |
| 5,718,664 | A | 2/1998 | Peck et al. |
| 5,833,701 | A | 11/1998 | Gordon |
| 5,990,382 | A | 11/1999 | Fox |
| 6,210,355 | B1 | 4/2001 | Edwards et al. |
| 6,267,769 | B1 * | 7/2001 | Truwit .......................... 606/130 |
| 6,342,053 | B1 | 1/2002 | Berry |
| 7,615,047 | B2 * | 11/2009 | Berna et al. ....................... 606/1 |
| 2001/0014771 | A1 | 8/2001 | Truwit et al. |

* cited by examiner

*Primary Examiner* — Ahmed Farah
(74) *Attorney, Agent, or Firm* — Stout, Uxa, Buyan & Mullins, LLP (57) ABSTRACT A shape and depth template for incisions with treatment tips, usable in treatments such as bone surgery, comprising a guiding body for a treatment tip provided with two mutually opposite end faces arranged at a preset distance and a lateral surface, one of the end faces being arrangeable at the treatment tip incision region and with a hole that of preset shape that passes there through from one end face to the other.

20 Claims, 8 Drawing Sheets

TREATMENT TIP INCISION TEMPLATE

CROSS-REFERENCE TO RELATED APPLICATIONS

This application is a continuation-in-part of U.S. application Ser. No. 10/843,476, filed May 12, 2004 now U.S. Pat. No. 7,615,047, which claims foreign priority to Italian Pat. App. PD2003A000102, filed May 15, 2003, the entire contents of both which are hereby incorporated by reference.

BACKGROUND OF THE INVENTION

1. Field of the Invention

The present invention relates to a shape and depth template for medical treatment (e.g. dosing, disrupting, ablating and/or cutting) applications such as the performance of cuts or incisions with treatment (e.g., laser) tips, particularly usable on tissue and, more particularly, usable in the context of exemplary applications such as hard tissue (e.g., bone) surgery.

The invention can be used particularly but not exclusively for providing osteotomy sites for dental implants.

The invention can also be applied in the execution of bone biopsies, the removal of calibrated bone samples for the most disparate uses in orthopedics, et cetera.

2. Description of Related Art

Until recently, the use of treatment-devices (e.g., lasers) in surgery was limited to the cutting of substantially soft tissues, since it was not possible to calibrate the power of, for instance, the laser for harder tissues.

Generally, if these devices (e.g., lasers) were applied to hard-tissue (e.g., bone) portions, they would burn said portions, with consequent death of the component cells.

Recently, new developments in medical treatment (e.g., laser) technologies have allowed devices such as lasers to perform incisions in bone tissues without burning them.

Scalpels with a laser tip are used for these incisions; the laser tips that are used can be different from one another. For example, the laser light of a laser tip can be conveyed by means of optical fibers, waveguide systems, or mirror systems; the laser of said scalpels may also be of the hydrokinetic type.

SUMMARY OF THE INVENTION

One aim of the present invention is to provide a shape and depth reference during the incision of biological tissues by means of treatment (e.g., laser) tips.

Within this aim, an object of the present invention is to provide a shape and depth template for incisions with treatment tips that is particularly usable in treatment applications such as bone surgery.

Another object of the present invention is to provide a shape and depth template for incisions with treatment tips, particularly usable in treatment applications such as bone surgery, that allows easy operation on the part of the surgeon.

A further object of the present invention is to provide a shape and depth template for treatments (e.g., incisions) with treatment tips, particularly usable, for instance, in bone surgery, that can in some examples allow for osteotomy sites of extreme precision, which comply with the physiology of the affected region.

A still further object of the present invention is to provide a shape and depth template for incisions with treatment tips, particularly usable, for instance, in bone surgery, that can in some instances allow for a certain elasticity in choosing the shapes and dimensions of the sites to be provided.

Another object of the present invention is to provide a shape and depth template for incisions with treatment tips, particularly usable, for instance, in bone surgery, that according to certain examples can be produced with known systems and technologies.

This aim and these and other objects that will become more apparent hereinafter are achieved by a shape and depth template for incisions with treatment tips that is particularly usable in treatment applications such as bone surgery, characterized in certain implementations as comprising a guiding body for a treatment tip that is delimited by two mutually opposite end faces arranged at a preset distance and by a lateral surface, one of said end faces being designed to be arranged at the region where incision with the treatment tip is to be performed, said guiding body having a hole that has a preset shape and passes through it from one end face to the other.

While the apparatus and method has or will be described for the sake of grammatical fluidity with functional explanations, it is to be expressly understood that the claims, unless indicated otherwise, are not to be construed as limited in any way by the construction of "means" or "steps" limitations, but are to be accorded the full scope of the meaning and equivalents of the definition provided by the claims under the judicial doctrine of equivalents.

Any feature or combination of features described or referenced herein are included within the scope of the present invention provided that the features included in any such combination are not mutually inconsistent as will be apparent from the context, this specification, and the knowledge of one skilled in the art. In addition, any feature or combination of features described or referenced may be specifically excluded from any embodiment of the present invention. For purposes of summarizing the present invention, certain aspects, advantages and novel features of the present invention are described or referenced. Of course, it is to be understood that not necessarily all such aspects, advantages or features will be embodied in any particular implementation of the present invention. Additional advantages and aspects of the present invention are apparent in the following detailed description and claims that follow.

BRIEF DESCRIPTION OF THE DRAWINGS

Further characteristics and advantages of the present invention will become more apparent from the following detailed description of preferred but not exclusive embodiments thereof, illustrated by way of non-limiting examples in the accompanying drawings, wherein.

DESCRIPTION OF THE PREFERRED EMBODIMENTS

Embodiments of the invention are now described and illustrated in the accompanying drawings, instances of which are to be interpreted to be to scale in some implementations while in other implementations, for each instance, not. In certain aspects, use of like or the same reference designators in the drawings and description refers to the same, similar or analogous components and/or elements, while according to other implementations the same use should not. According to certain implementations, use of directional terms, such as, top, bottom, left, right, up, down, over, above, below, beneath, rear, and front, are to be construed literally, while in other implementations the same use should not. The present invention may be practiced in conjunction with various techniques that are conventionally used in the art, and only so much of the commonly practiced process steps are included herein as are necessary to provide an understanding of the present invention. The present invention has applicability in the field of medical devices and processes in general. For illustrative purposes, however, the following description pertains to treatment devices and related methods of use.

With reference to the figures, a shape and depth template for incisions with treatment tips according to an exemplary embodiment is designated in the illustrated example by the reference numeral 10. As embodied herein, templates of the invention can have medical treatment (e.g., dosing, disrupting, ablating and/or cutting) applications such as the performance of cuts or incisions with treatment (e.g., laser) tips. They can be particularly usable on tissue and, more particularly, can be usable in the context of exemplary applications such as in hard tissue (e.g., bone) surgery, according to certain features of the invention.

Figure 1:
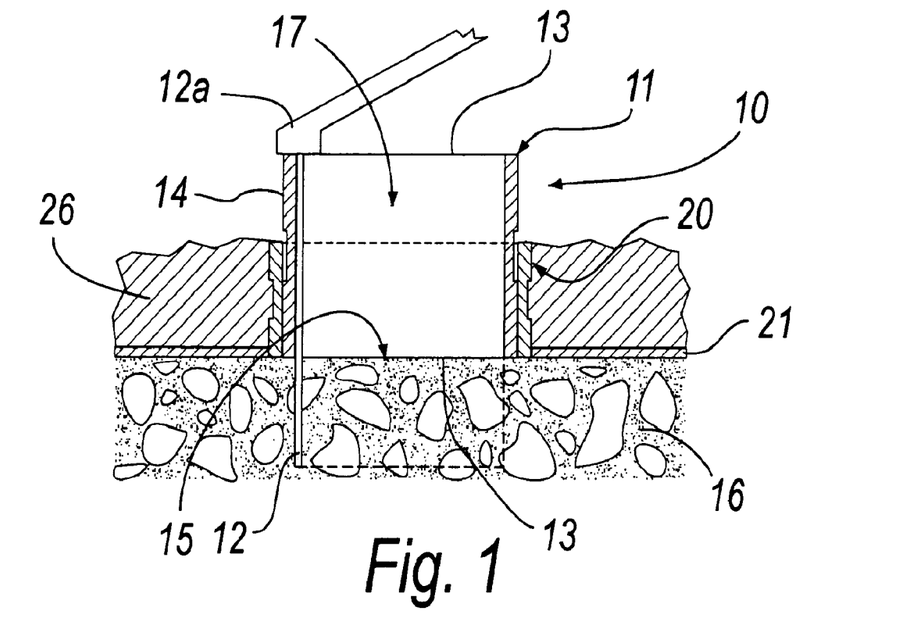
FIG. 1 is a sectional front view of a template according to the invention, applied to a gingival bone, illustrating a treatment scalpel during incision.
Figure 2:
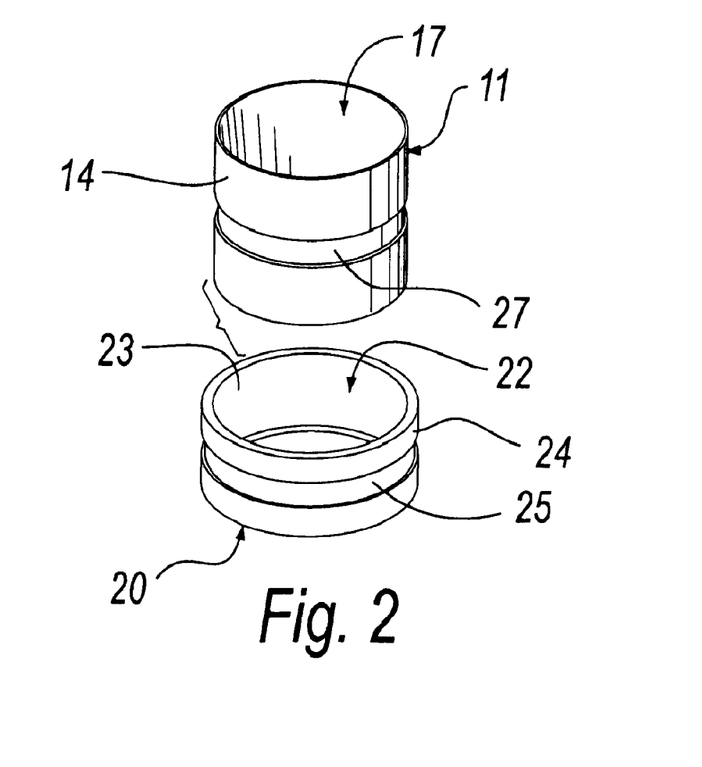
FIG. 2 is an exploded perspective view of a template according to the invention.

The template 10 is exemplified comprising a guiding body 11 for a treatment tip (of preset length), designated by the reference numeral 12 in FIG. 1. The treatment tip may be configured to emit one or more of, in no order of preference, electromagnetic (e.g., laser) energy, abrasive particles (e.g., silica, aluminum oxide, or a baking soda mixture propelled by compressed air) and/or acoustic energy (e.g., vibrations, such as sonic, supersonic and/or ultrasonic emissions, sound energy that may have a frequency greater than 20 kHz, high-intensity focused or applied forms of the preceding, and/or other acoustic means and equivalents thereof).

Exemplary acoustic energy emitting (e.g., sonic cutting/ablating) treatment tips can comprise and/or utilize, in whole or in part, in any combination with any other technology disclosed or referenced herein, to the extent compatible or modifiable to be compatible and/or not mutually exclusive, that of (a) micro-vibrating sonic movement of air-driven handpieces (e.g., by Sonicflex kayo); and (b) sonosurgery bonetips "sonic" instruments made by Komet (e.g., by Gebr. Basseler DE, provided in any of 3 shapes for operation within the mouth as formed with very thin incision sections (0.2 mm), all of which is incorporated herein by reference. (See Agabiti, Ivo "ERE (Edentulous Ridge Expansion) technique in two stages," Apr. 23b2009, published at http://en.zerodonto.com/2009/04/sonosurgery-komet-sonic-tips.html or http://tinyurl.com/y9o8lkd.) Further information incorporated herein by reference for the same purposes is (c) pages 11 et. seq., beginning with "Sonosurgery® SFS," of Innovazioni 2009 IT, published at http://www.komet.it/fileadmin/images/innovations/Innovazioni_09_IT_GB.pdf or http://tinyurl.com/ybj3lds.

Figure 11:
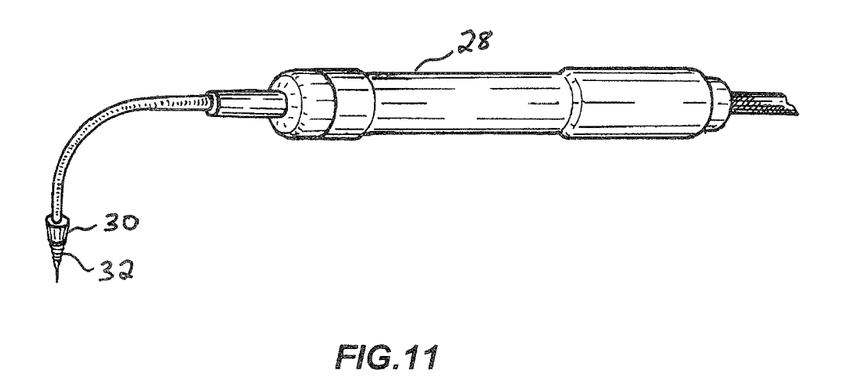
FIG. 11 is a schematical view of a first embodiment of a sonic or ultrasonic tip having a conical or tapered shape for the use with the templates according to the present invention.
Figure 12:
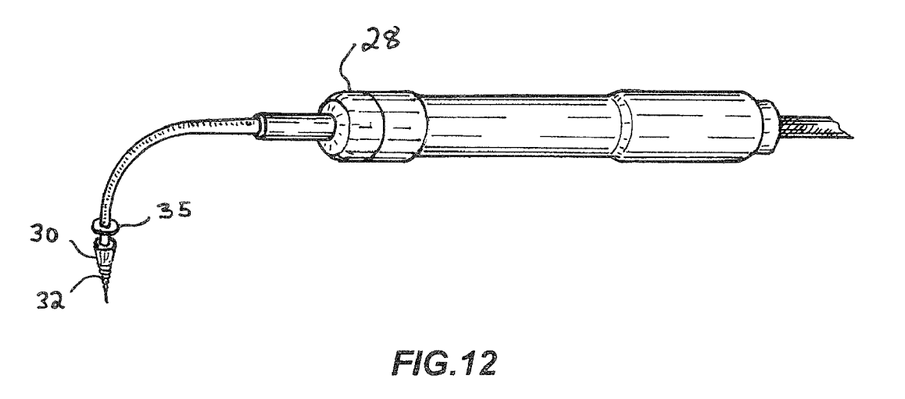
FIG. 12 is a schematical view of a second embodiment of a sonic or ultrasonic tip having a conical or tapered shape, with a stop area, for the use with the templates according to the present invention.

Furthermore, as shown in FIGS. 11 and 12 any of such acoustic energy emitting treatment tips can comprise and/or utilize, as (d), a conical, oral and/or tapered sonic or ultrasonic tip (e.g., for the making of non cylindrical bores). Each of the tips can comprise, for instance, a smooth surface 30, which may, in some implementations, facilitate a slidable/movable fit within the guiding body 11 of the template 10, and may further comprise a working surface 32 for emitting energy and/or otherwise affecting/facilitating, for example, boring. In certain embodiments, the working surface 32 may comprise an abrasive surface. The embodiment of FIG. 12 comprises a stop area 35, for facilitating treatments which may require or benefit from, for example, a limited or predetermined depth.

Figure 13:
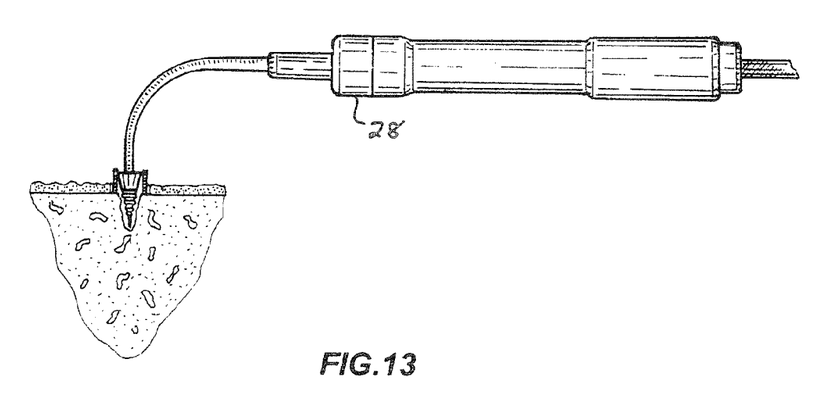
FIGS. 13 and 14 are schematical views of bone ablating steps using the first embodiment of a sonic or ultrasonic tip of FIG. 11.
Figure 14:
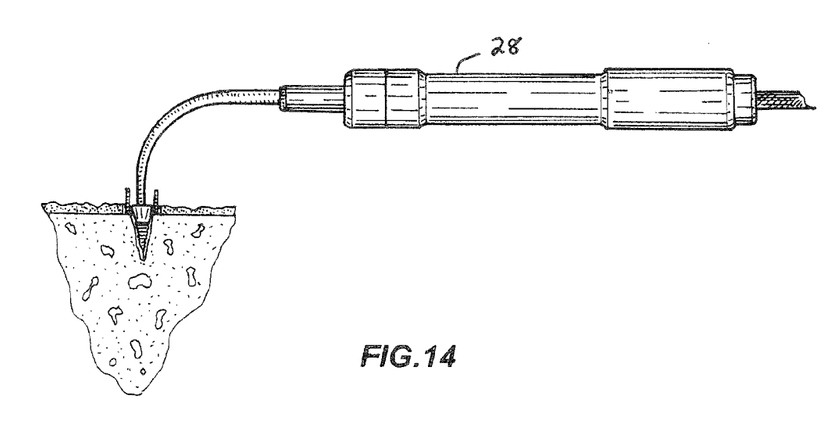
Figure 15A:
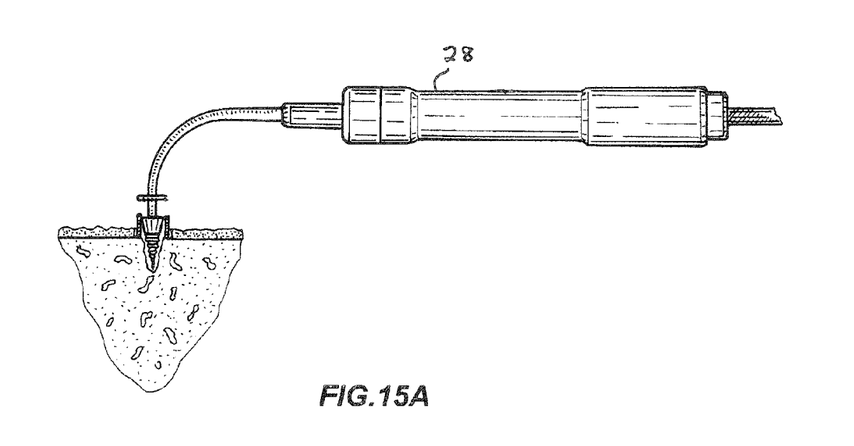
FIGS. 15A and 15B are schematical views of different bone ablating steps using the second embodiment of a sonic or ultrasonic tip of FIG. 12.
Figure 15B:
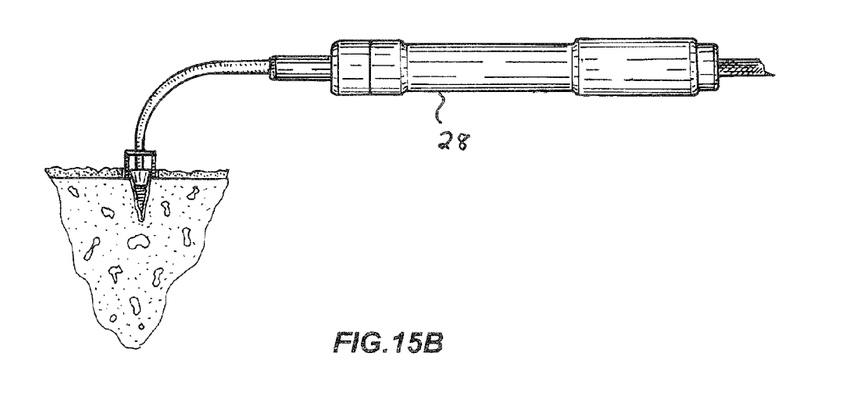

FIGS. 13 and 14 depict a first sequence of operation, using, for example, the configuration of FIG. 11, and FIGS. 15A and 15B depict a second sequence of operation, using, for example, the configuration of FIG. 12.

Emissions can in certain implementations be accomplished under control or by aid of (e) a circuit such as a microprocessor. The microprocessor can be programmed to vary the timings, powers, distributions, and/or other characteristics of the emissions, in accordance with desired cuts or treatments to be achieved. Additionally, such parameters may be varied/controlled in accordance with the surface being treated/disrupted (for example, particular type or condition of bone and/or soft tissue). In any of the disclosed or referenced embodiments, as well as additional embodiments as would be apparent in view of this disclosure, a surface-profile imager/generator can be implemented to provide a computer generated model of a surface being scanned, as or at least partly analogous to that disclosed in U.S. Pat. No. 5,588,428. A visible beam, for example, may be used to collect profile information of the target to be treated. Emissions from the treatment tip can be scanned accordingly, with for example the amount and/or properties of the emissions being varied in accordance with different areas and/or desired treatments to be imparted.

In the disclosed or referenced embodiments, as well as additional embodiments as would be apparent in view of this disclosure, actual emitting orifices (e.g., waveguides such as optical fiber) can be scanned using a motor assembly. Other embodiments can also or alternatively comprise scanning using reflectors and/or focusing optics, as known in the art. U.S. Pat. No. 5,624,434, and patents and references cited therein, disclose apparatuses which scan using dynamically controlled deflectors, the contents of which are expressly incorporated herein by reference. In other embodiments, similar technology may be incorporated in (f) hand-held pieces, wherein a few or substantially all of the parts therein are fixed and/or do not move, and/or wherein the handpiece is moved, also or instead.

The guiding body 11 is formed by two mutually opposite end faces 13, which are arranged at a standardized preset distance from each other, as will become better apparent hereinafter, and by a lateral surface 14.

One of the end faces 13 is to be arranged at a region 15 where incision with the treatment tip 12 is to be performed.

For example, FIG. 1 illustrates a gingival bone 16 to which the template 10 according to the invention, useful for providing an osteotomy site for dental implants, is applied.

In this embodiment, the lateral surface 14 of the guiding body 11 has a substantially cylindrical shape.

The guiding body 11 has a hole 17 that has a preset shape and passes through it from one end face to the other.

In this embodiment, the hole 17, which is coaxial to the cylindrical extension of the entire guiding body 11, has a circular cross-section.

In other embodiments, shown in FIGS. 5-10, the hole 17 has a cross-section that is respectively triangular, elliptical, figure-of-eight (two-lobe), square, rectangular, semicircular, in all of which any corners are radiused.

Figures 3, 4:
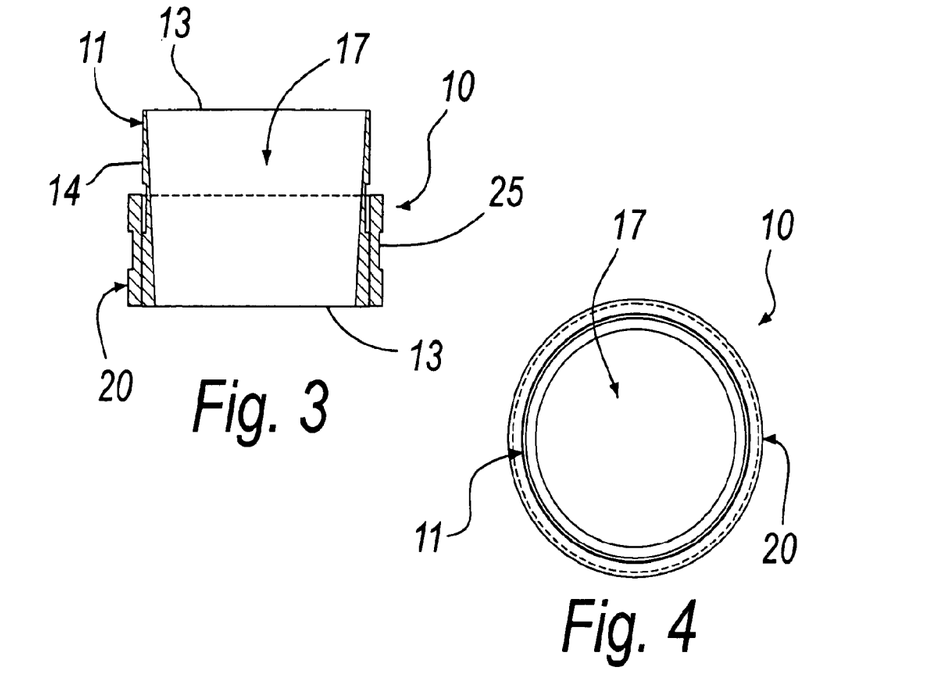
FIG. 3 is a sectional front view of a template according to the invention in an alternative embodiment with respect to the shape of FIG. 1.
FIG. 4 is a plan view of the template of FIG. 3.
Figure 5:
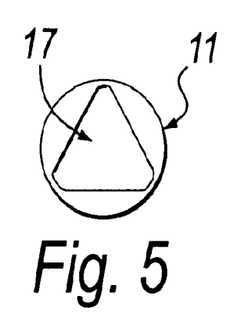
FIGS. 5-10 are five plan views of a corresponding number of alternative embodiments of the template according to the invention.
Figure 6:
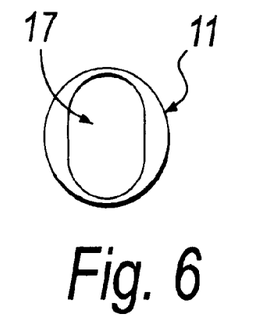
Figure 7:
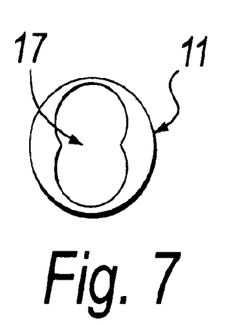
Figure 8:
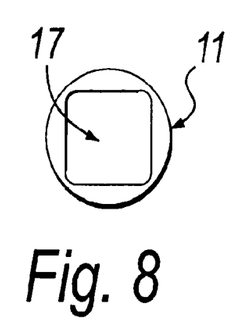
Figure 9:
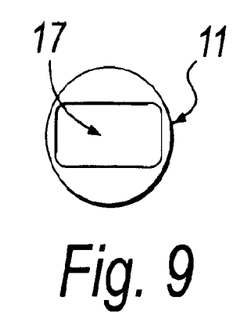
Figure 10:
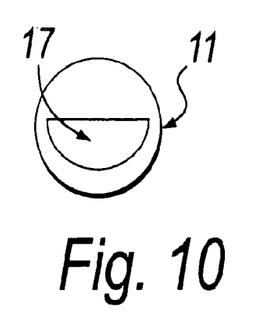

The hole 17 further has, depending on the type of use, a straight wall shape (see FIG. 1), or a shape that tapers from the outside toward said incision region (which corresponds to the bone to be cut or ablated), as shown in FIGS. 3 and 4; in this last case, the hole 17 having a circular cross-section has a substantially conical shape, preferably a straight conical shape.

The template 10 also comprises a jacket 20 that acts as a reference for the guiding body 11 and is designed to be rigidly fixed, by way of a supporting structure 21, at the incision region 15.

The jacket 20 has a through hole 22 that is formed by an internal surface 23 that is shaped complementarily to the lateral surface 14 of the guiding body 11 and is therefore cylindrical.

In particular, in this embodiment the jacket 20 has an outer surface 24 that has a substantially cylindrical shape.

Advantageously, on the outer surface 24 of the jacket 20 there is a first annular groove 25 to allow the jacket 20 to grip a supporting matrix 26 provided on the supporting structure 21 arranged in the incision region 15.

A second annular groove 27 is formed at an outer region of the lateral surface 14 of the guiding body 11 to allow to grip the supporting matrix if the guiding body 11 is applied without the jacket 20, as explained hereinafter.

The use of the template is as follows.

Consider for example the case of the execution of an osteotomy site for the insertion of a dental implant.

After determining the position in which the site is to be provided on the alveolar bone of the patient, an impression tray of the dental arch is performed.

The supporting structure 21 for the template 20 is provided by using the spatial references of said impression tray; said template is therefore positioned in the correct location for providing the site.

A matrix of resin 26 is arranged on the supporting structure 21 and stably locks the template 20 in position.

In particular, the jacket 20 is embedded in the matrix 26.

The guiding body 11 is inserted in the hole of the jacket so as to rest one end face of the guiding body on the surface, or tissue, or hard tissue such as bone, to be treated (e.g., cut or ablated).

At this point, the treatment tip 12, which protrudes from the treatment head 12 of a treatment scalpel, is inserted in the hole 17.

The treatment tip 12 must follow the internal surface of the hole 17 so as to provide the contour of the site.

The depth of the site is ensured by the fact that the height of the guiding body 11 is known and so is the length of the treatment tip; at the most, the treatment head can rest against the edge of the guiding body, thus ensuring the chosen depth of incision.

For this reason, guiding bodies having different heights and optional internal tapers are provided according to a series of predefined sizes.

For example, it is possible to provide templates in which, depending on the length of the guiding body, a particular inclination of the internal surface of the hole 17 is associated; moreover, the treatment tip may also be adjusted in order to assume certain preset lengths, thus increasing the adjustment of the incision depth.

Having a through hole with an internal taper on the guiding body allows to provide conical sites.

The various shapes of the hole of the guiding body cited above (which can be tapered or not), allow to provide sites of an appropriate shape.

For example, the figure-of-eight shape is typical of the implantation of a molar, the triangular shape is typical of a canine, the ellipsoidal shape is typical of a premolar, and so forth; in this manner, it is possible to provide sites that comply with the original anatomy of the affected region.

It is extremely advantageous to use a jacket that is fixed in the matrix and a removable guiding body; in this manner one has great flexibility in choosing the sizes for providing the site. One can for example decide to use at the last minute, before the operation, a guiding body that is different from the preset one, since it is believed to be more suitable after visual assessment "in the field;" in this manner, one avoids having to remake the supporting structure.

Moreover, it is possible to recover the guiding body once the operation has been completed and to discard only the jacket embedded in the matrix of the supporting structure, said jacket being associable with all the models of various sizes of the guiding body.

The use of said template may be the most disparate, from the above described provision of osteotomy sites for dental implants to the calibrated removal of tissue (e.g., hard tissue such as bone) portions in various parts of the body for the most disparate reasons, biopsies, removal of material to be used in other regions, et cetera.

In practice it has been found that the invention thus described achieves the intended aim and objects; in particular, the present invention provides a shape and depth template for incisions with treatment tips, particularly usable, for example, in bone surgery thereby allowing for osteotomy sites and bone samples having precise shapes and dimensions.

As shown in FIGS. 13 and 14, the treatment tip is a supersonic tip according to the embodiment of FIG. 11, the tip being suitable to cooperate with the templates of the present invention for the making of bores and/or ablating bones. The figures show the different operating steps, starting from the drilling of a central bore in the bone and subsequently by removing with an ablating operation the bone material following the template shape.

On the other hand, and as shown in FIGS. 15A and 15B, the treatment tip may be a supersonic tip according to the embodiment of FIG. 12, the tip being suitable to cooperate with the templates of the present invention for the sake of making bores and/or ablating bones. The figures show the different operating steps, starting from the ablating of a central bore in the bone and subsequently by removing with an ablating operation the bone material following the template shape, by abutting the tip sides onto the jacket.

Figure 16:
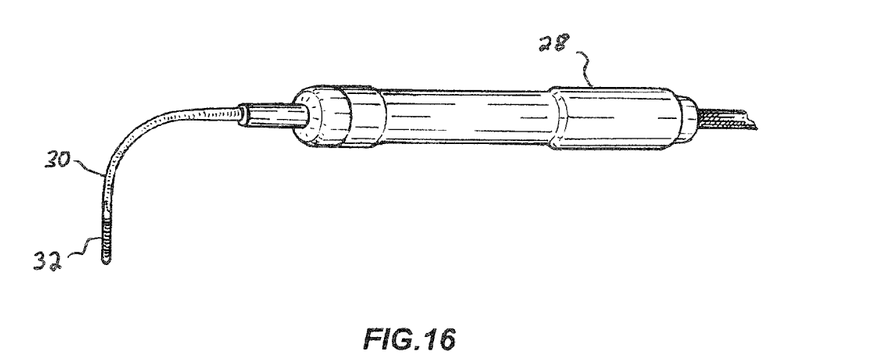
FIGS. 16-18 are schematic views of another set of steps for boring or ablating bone with another embodiment of a sonic or ultrasonic tip having a cylindrical shape, and suitable for being used with the jackets/templates according to the present invention.
Figure 17:
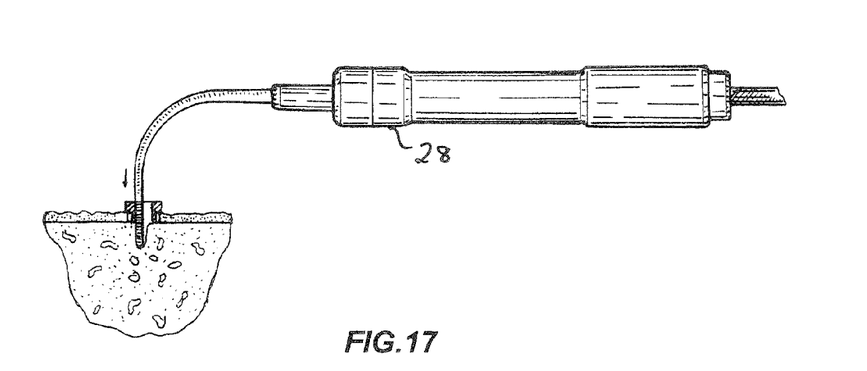
Figure 18:
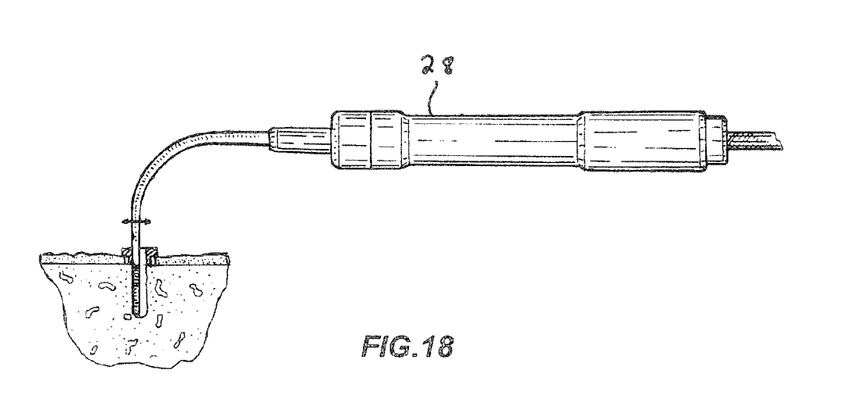

FIGS. 16-18 elucidate a set of steps for boring or ablating bone with another embodiment of a sonic or ultrasonic tip having one or more of, for example but not by way of limitation, a cylindrical, non-tapered, or oval shape, and suitable for being used with the jackets/templates according to the present invention As shown in FIG. 16, the treatment tip may be a supersonic tip suitable to cooperate with the templates of the present invention for the sake of making bores and/or ablating bones. According to the illustrated version of this embodiment, the tip can comprise a straight cylindrical shape with a working (e.g., abrasive and/or emitting) surface 32 and a non-working surface 30. The non-working surface can, but need not necessarily be, smooth, due, for instance, to its relatively small diameter as compared to the diameter of the hole 17 of the guiding body 11 of the template 10. The figures show a number of operating steps, starting from the drilling of a central bore in the bone and continuing to removing with an ablating operation the bone material following the template shape. According to the illustrated version of this embodiment, the tip can comprise a relatively small diameter as compared to the diameter of the hole 17 of the guiding body 11 of the template 10, whereby, for instance, the tip can (e.g., in an exemplary but not limiting application) penetrate and be advanced into the tissue (e.g., bone) bone without it even touching the guiding body 11. For instance, according to a few but not all implementations the tip need not snugly fit within the hole, thus providing, for example, a degree of flexibility or maneuverability to the process. In various implementations, however, such as that depicted in FIG. 18, the inner surface of the guiding body 11 can still (e.g., at the user's option) be used as a guide or template by way of, for example, movement of the tip in a direction transverse (c.f., arrow in FIG. 18) to the direction of insertion (c.f., arrow in FIG. 17) so that, for example, contact is made and/or a longitudinal length of the tip rests against the inner surface of the guiding body 11. For instance, in an implementation comprising, as an example, a working surface 32 having an abrasive characteristic, the tip may be advanced distally through the guiding body 11 until the working surface 32 is no longer within the hole 17 (c.f., FIG. 18), at which time a user may maneuver the smooth surface 30 into contact (e.g., sliding engagement) with the inner surface of the guiding body 11.

Figure 19A:
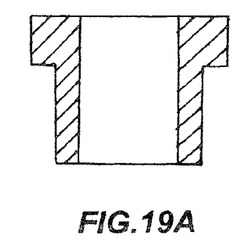
FIGS. 19A-19C are sectional views of different embodiments of jackets/templates for the control and metering of the height/depth of the boring or ablating bone steps according to the present invention.
Figure 19B:
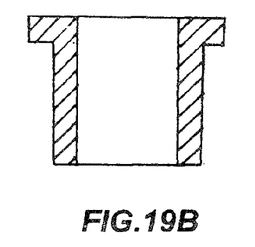
Figure 19C:
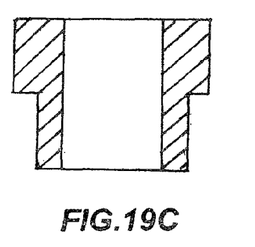
Figure 20:
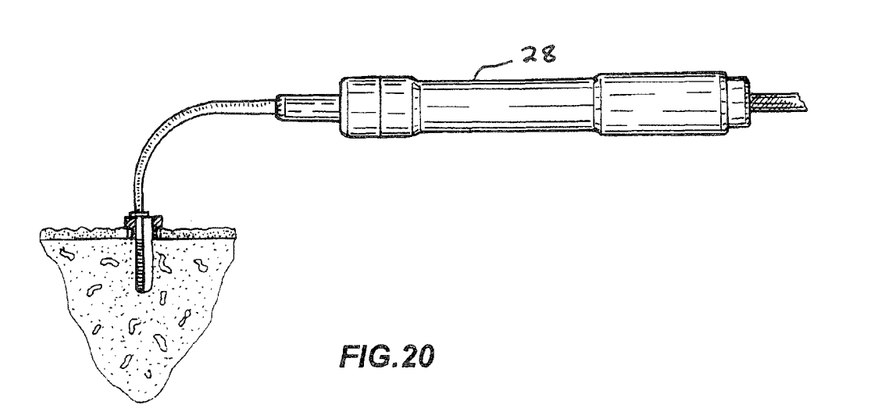
FIG. 20 is a schematical view of a sonic or ultrasonic cylindrical tip using an embodiment of a template of FIGS. 19A-19C.
Figure 21:
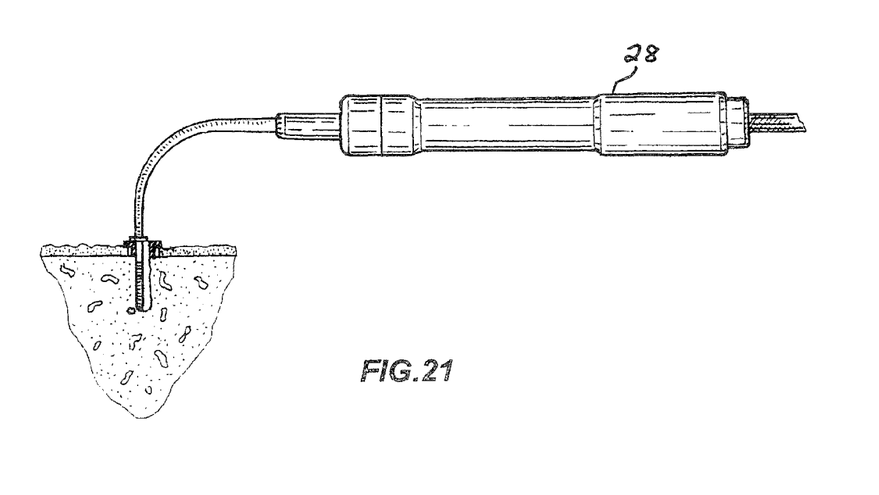
FIG. 21 is a schematical view of another sonic or ultrasonic cylindrical tip using another embodiment of a template of FIGS. 19A-19C.

As shown in FIGS. 19A-19C, there are provided according to the present invention different shapes and/or different depths (e.g., different shoulder heights) of the jackets/templates for the treatment tip. According to the present invention, and as shown in FIGS. 20 and 21, a supersonic tip suitable to cooperate with the jackets/templates shown in FIGS. 19A-19C of the present invention may realize the making of bores and/or ablating bones by controlling the depth of the former. The figures show different operating steps, starting from a drilling of a central bore in the bone and followed by removing with an ablating operation the bone material following the template shape with a controlled depth by final abutment of the treatment tip onto the jacket/template edge specifically chosen in a depth value.

Figure 22:
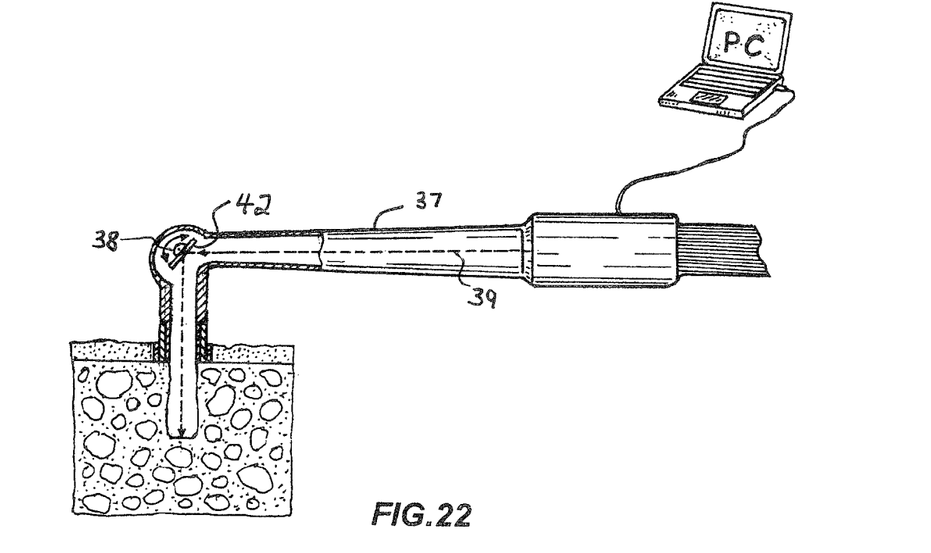
FIG. 22 is a schematical view of a boring or ablating bone step with an embodiment of a laser microscanner for the use with the templates according to the present invention.

With reference to FIG. 22, a scanning/ablating and/or boring implementation 37 may perform, using, for example, a microscanner 38, a cutting operation, whereby according to a typical but not limiting embodiment a cutting laser 39 can be driven through or under partial or full control of the microscanner 38. For instance, an electromagnetically controlled mirror 42 can be positioned on the template whereby the scanning/ablating cutting operation is obtained without a fiber laser tool (e.g., fiber optic) needing to be inserted into the tissue.

Figure 23:
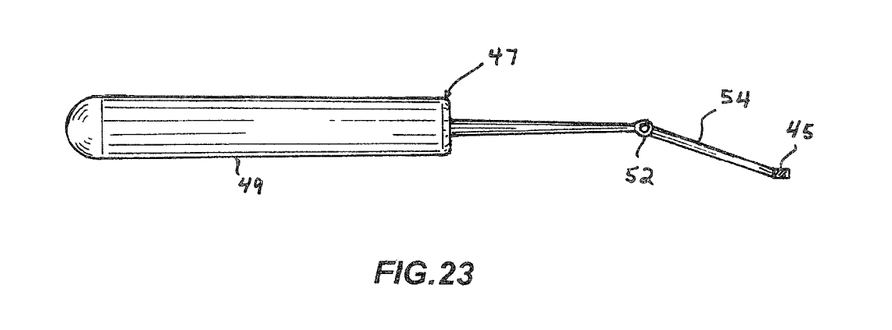
FIG. 23 is a schematical view of a template hand holder tool according to the present invention.

As shown in FIG. 23, according to the present invention the template 45 may be held via a holding tool 47 which incorporates a handpiece 49 having a projecting part where a joint connection 52 is provided and where a holding rod 54 is connected thereto. The holding rod 54 foresees (e.g., facilitates) connecting projections for the secure connection of one or more predetermined templates at the distal end thereof.

The invention thus conceived is susceptible of numerous modifications and variations, all of which are within the scope of the appended claims; all the details may further be replaced with other technically equivalent elements.

In practice, the materials used, as well as the contingent shapes and dimensions, may be any according to requirements and to the state of the art.

Although the disclosure herein refers to certain illustrated embodiments, it is to be understood that these embodiments have been presented by way of example rather than limitation. Corresponding or related structure and methods specifically contemplated, disclosed and claimed herein as part of this invention, to the extent not mutually inconsistent as will be apparent from the context, this specification, and the knowledge of one skilled in the art, including, modifications thereto, which may be, in whole or in part, (i) operable and/or constructed with, (ii) modified by one skilled in the art to be operable and/or constructed with, and/or (iii) implemented/made/used with or in combination with, any parts of the present invention according to this disclosure, include the subject matter of any one or more of the following claims, in any permutation and/or combination and/or may further include one or more of a sonic or supersonic treatment tip (e.g., FIGS. 16-18), a sonic or supersonic oval or tapered tip (e.g., FIGS. 11-15), a height control jacket/template (e.g., FIGS. 19A-19C), a sonic or supersonic treatment tip with an abutment to cooperate with jackets such as those of FIGS. 19A-19C (e.g., FIGS. 20-21), a laser microscanner for the ablating operation (e.g., FIG. 22), and a handpiece template holding set (e.g., FIG. 23). The intent accompanying this disclosure is to have such embodiments construed in conjunction with the knowledge of one skilled in the art to cover all modifications, variations, combinations, permutations, omissions, substitutions, alternatives, and equivalents of the embodiments, to the extent not mutually exclusive, as may fall within the spirit and scope of the invention as limited only by the appended claims.

What is claimed is:

1. A shape and depth template for incisions with treatment tips, comprising:
  a guiding body for guiding a treatment tip, said guiding body being delimited by two mutually opposite end faces arranged at a preset distance and by a lateral surface, a tissue-contacting one of said end faces being arrangeable so as to rest on a region where incision is to be performed by a treatment tip, said guiding body having a hole that passes through the guiding body from one of said end faces to the opposite one and that has a preset shape providing a contour to be followed by said treatment tip;

a jacket that forms a reference for said guiding body, said jacket comprising a first end surface, a mutually opposite second end surface, which surrounds said tissue contact end, an outer surface and a through hole formed by an internal surface thereof that is shaped complementarily to said lateral surface; and a supporting structure having an inner engaging structure which surrounds the second end surface, which is shaped complementarily to said outer surface at said second end surface, and which is shaped to contact substantially all of said jacket at said region and to enable rigid fixation of said jacket where treatment tip incision is performed in an orientation such that said second end surface and said tissue-contacting end face are both held to rest upon the region, said supporting structure further having a perimeter extending radially outwardly from the engaging structure and oriented to fit over tissue surrounding the region.

2. The template of claim 1, further comprising surface indentations on said lateral and outer surfaces.

3. The template of claim 2, wherein said internal surface of said through hole of said jacket and said lateral surface of said guiding body are substantially cylindrical.

4. The template of claim 2, wherein said hole is shaped so as to taper from one end face of the guiding body toward the opposite end thereof where said treatment tip incision region lays.

5. The template of claim 4, wherein said hole has a substantially straight conical shape.

6. The template of claim 2, further comprising a first annular groove formed on an outer lateral surface of said jacket.

7. The template of claim 6, further comprising a second annular groove formed at an outer region of said lateral surface of said guiding body.

8. The template of claim 1, wherein said hole is substantially straight wall shaped.

9. The template of claim 1, wherein said hole has a substantially circular cross-section.

10. The template of claim 1, wherein said hole has a substantially ellipsoidal cross-sectional shape.

11. The template of claim 1, wherein said hole has a substantially figure-of-eight cross-sectional shape.

12. The template of claim 1, wherein said hole has a substantially semicircular cross-sectional shape.

13. The template of claim 1, wherein said hole has a substantially triangular cross-sectional shape with radiused corners.

14. The template of claim 1, wherein said hole has a substantially square cross-sectional shape with radiused corners.

15. The template of claim 1, wherein said hole has a substantially rectangular cross-sectional shape with radiused corners.

16. The template of claim 1, wherein said treatment tip is arranged to emit sonic cutting or ablating energy.

17. The template of claim 1, wherein said treatment tip is arranged to emit ultrasonic cutting and ablating energy.

18. The template of claim 1, wherein said treatment tip is arranged to emit one or more of supersonic and ultrasonic energy suitable for cutting or ablating hard tissue.

19. The template of claim 18, wherein said hard tissue is bone.

20. The template of claim 1, wherein said treatment tip is arranged to emit laser energy suitable for cutting and ablating bone.

* * * * *